United States Patent [19]

Klausmeier et al.

[11] 4,287,129
[45] Sep. 1, 1981

[54] SYNTHESIS OF 1α-HYDROXY-7-DEHYDROSTEROIDS

[75] Inventors: William H. Klausmeier, Elmhurst; Richard L. Johnson, Northlake; Arnold L. Hirsch, Oak Park, all of Ill.

[73] Assignee: Diamond Shamrock Corp., Dallas, Tex.

[21] Appl. No.: 172,925

[22] Filed: Jul. 28, 1980

[51] Int. Cl.³ ............................................. C07J 9/00
[52] U.S. Cl. ........................... 260/397.1; 260/397.2; 260/239.5
[58] Field of Search ................ /Steroids MS File; 260/397.2, 239.5, 397.1

[56] References Cited

U.S. PATENT DOCUMENTS

| | | | |
|---|---|---|---|
| 4,022,768 | 5/1977 | Matsunaga et al. | 260/239.5 |
| 4,069,321 | 11/1978 | Jones et al. | 260/397.2 |
| 4,188,322 | 2/1980 | Castelli et al. | 260/239.55 R |

*Primary Examiner*—Elbert L. Roberts
*Attorney, Agent, or Firm*—Neal T. Levin

[57] ABSTRACT

Enol acetylation is carried out on a variety of 1,4,6-trien-3-ones to form 1,3,5,7 tetraene structures from which 1α-hydroxy-7-dehydro steroids are obtained.

The compounds are intermediates used in the preparation of vitamin $D_3$ metabolites such as 1α,25-dihydroxyvitamin $D_3$ and 1α-hydroxyvitamin $D_3$.

14 Claims, No Drawings

SYNTHESIS OF 1α-HYDROXY-7-DEHYDROSTEROIDS

BACKGROUND OF THE INVENTION

1. Field of the Invention

This invention relates to the preparation of 1α-hydroxy-7-dehydrosteroids and new intermediates obtained thereby.

2. Description of the Prior Art

The conventional synthesis of vitamin $D_3$ involves conversion of cholesterol to 7-dehydrocholesterol and subsequent irradiation of this diene with ultraviolet light to photochemically convert it to pre-vitamin $D_3$, which is thermally rearranged to cholecalciferol (cis-vitamin $D_3$).

Recent discoveries have shown that vitamin $D_3$ is converted to 25-hydroxyvitamin $D_3$ in the kidney and this product subsequently undergoes 1α-hydroxylation in the liver to form 1α,25-dihydroxy-vitamin $D_3$. This is the most active form of vitamin $D_3$ that has been found.

Much work has been done in an effort to synthetically prepare the various derivatives of vitamin $D_3$. Among the procedures developed, most have been concerned with sequentially introducing the desired functional groups into the steroid nucleus, i.e., the 25-hydroxy group, the 1α-hydroxy group, the 7-ene functionality, etc. Attempts also have been made to introduce the 1α-hydroxy group and the 7-ene functionality in the same set of reactions. For example, the following two routes have been described.

However, both routes possess serious drawbacks. In Route A, the lithium reduction is not a high yield (55% in the reduction) as also is the case for the allylic bromination-dehydrobromination. See Sato et al, Chem. Pharm. Bull., 2933, 26 (1978) and U.S. Pat. No. 3,993,675, Uskokovic et al, Nov. 23, 1976. In Route B, the deconjugation procedure is quite unreliable and low-yielding. See Ochi et al, J. Chem. Soc. Perkin I, 165 (1979); Kaneko et al, Tetrahedron 30, 2701 (1974) and Guest et al, J. Chem. Soc. Perkin I, 1695 (1979). With the large number of steps needed to complete these sequences, low yields are especially undesirable.

Another method for the generation of the 5,7-diene is by formation of the enol acetate of a $\Delta^{4,6}$-3-ketone:

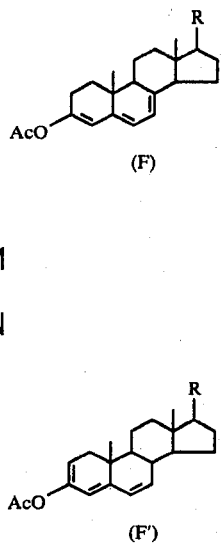

However, a serious drawback to this approach is that the 4,6-diene-3-one also enolizes in the other direction forming undesired $\Delta^{2,4,6}$ side product (F') in admixture with the desired $\Delta^{3,5,7}$ product (F). Efforts at directing enolization in the desired direction have met with only

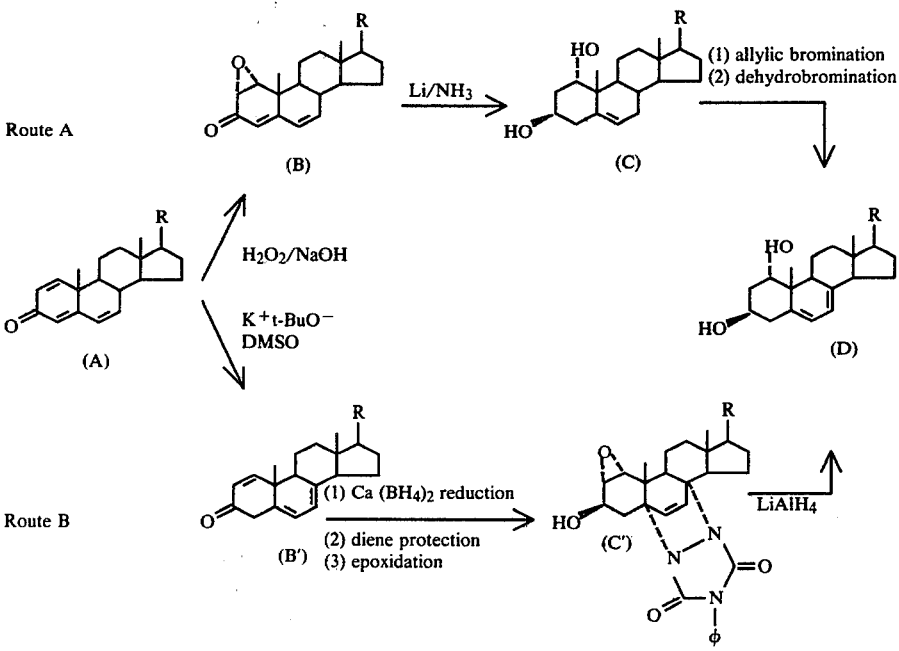

partial success. See Dauben et al, J. Amer. Chem. Soc., 73, 4496 (1951) and Zderic et al, Steroids, 1, 233 (1963).

Reference is made to Velluz et al, Bull. Soc. Chem. Fr. 1289 (1957) who disclose yields from enol acetylation of 90% and 83% (Compounds IV and VII respectively). However, these yields are obtained by acylating 19-nor steroids, i.e., steroids having no methyl group attached to the 10 position. Enolization to the $\Delta^{3,5,7}$ triene is highly favored where the 19-methyl group is absent.

In another instance Whalley et al, J. Chem. Soc. Perkin I, 820 (1977), starting with the 7-ene functionality, i.e., with 5α-cholest-7-en-3β-ol (G), prepared cholesta-1,3,5,7-tetraen-3-yl acetate (I) via oxidation, bromination, dehydrobromination and enol acetylation and from this prepared 1α-hydroxy-7-dehydrocholesterol (J).

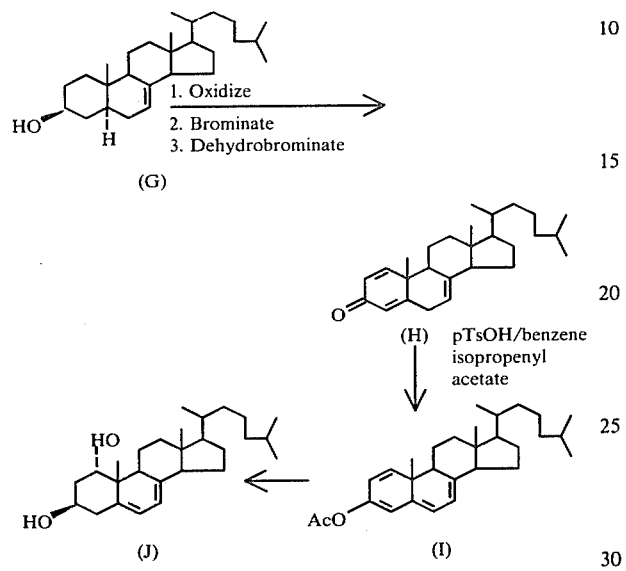

However, application of this procedure to substrates possessing 25-hydroxyl or ester group often leads to by-products due to elimination in the side-chain caused by presence of a strong acid catalyst. Further, the initial substrate, 5α-cholest-7-en-3β-ol (G) is itself produced by hydrogenation of 7-dehydrocholesterol (Fieser et al, J. Amer. Chem Soc., 75, 121 (1953)) which itself contains the 5,7-diene system and, therefore, is not a practical starting point for a commercially feasible synthesis of the same 5,7-diene system.

SUMMARY OF THE INVENTION

According to the invention, enol acetylation (enol esterification) is carried out on 1,4,6-trien-3-ones as shown below to form the corresponding enol acetate (1,3,5,7-tetraene-3-yl acetate).

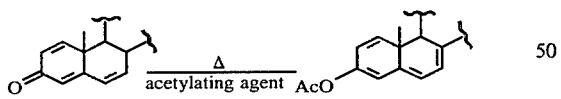

By starting with the 1,4,6-trien-3-one, the desired 1,3,5,7-tetraene-3-yl acetate is obtained in high yields, i.e., 80% to the exclusion of side products such as the undesired 2,4,6-trien-3-yl acetate. Formation of the latter is prevented since the ketone on the 3-position of the 1,4,6-trien-3-one is not enolizable towards the 2-position as in the case of the $\Delta^{4,6}$ ketone (F').

Additionally, the enol acetate is considerably more stable than the 1,5,7-trien-3-one obtained by the deconjugation procedure described above. Further, the deconjugation procedure has not been able to be scaled up above one gram, while enol acetylation works just as well on a large scale as on a small scale. Where pyridine is present, it buffers against the presence of acid and, therefore, the reaction can be carried out where acid sensitive groups are present and no dehydration is detected. Thus, the present process has the advantage of allowing introduction of the 7-dehydro- and 1α-hydroxy-functions in the same set of reactions. More importantly, this is accomplished in higher yield than can be done with known methods.

A preferred class of 1,4,6-trien-ones is shown below:

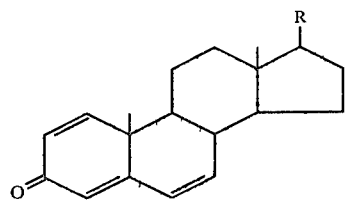

where:

R is 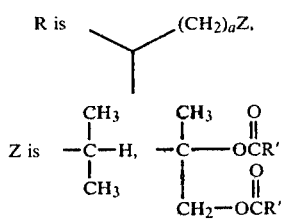 (CH$_2$)$_a$Z,

Z is $-\overset{\overset{\displaystyle CH_3}{|}}{\underset{\underset{\displaystyle CH_3}{|}}{C}}-H$, $-\overset{\overset{\displaystyle CH_3}{|}}{\underset{\underset{\displaystyle CH_2-OCR'}{|}}{C}}-\overset{\overset{\displaystyle O}{\|}}{OCR'}$ and where Z is the above, a is 3,

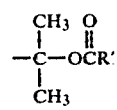

and where Z is the above, a is 0, 1, 2 or 3,

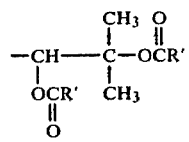

and where Z is the above, a is 2, and

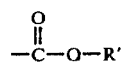

and where Z is the above, a is 0, 1, 2 or 3, and R' is hydrogen, alkyl such as methyl, ethyl, propyl, isopropyl, butyl, etc. or aryl such as phenyl.

The 1,4,6-trien-3-one compounds are obtained by oxidation of 3-hydroxy-5-enes, i.e.,

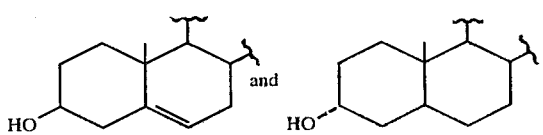

or other material which can be converted to 1,4,6-trien-3-ones.

Exemplary of compounds which can be used as substrates are the following:

I. Bile Acids

3β-Hydroxy cholenic acid
3α-Hydroxy cholanic acid
3β-Hydroxy norcholenic acid
3β-Hydroxy dinorcholenic acid
3β-Hydroxy homocholenic acid

II. Cholesterols

25-Hydroxycholesterol
24,25-Dihydroxycholesterol
25,26-Dihydroxycholesterol

The cholesta-1,3,5,7-tetraene-3-yl acetates so obtained can be used, employing reactions well described in the literature, such as the reaction sequence of Whalley et al, to prepare 1α-hydroxy-7 dehydrocholesterols.

For example, starting with the compounds previously listed they first undergo oxidation, then enol acetylation and finally through established procedures form such compounds as 1α-hydroxy-7-dehydrocholesterol and 1α,25-dihydroxy-7-dehydrocholesterol. These compounds in turn can be used to prepare 1α-hydroxyvitamin $D_3$ and 1α,25-dihydroxyvitamin $D_3$, respectively, by known procedures.

The following sequence of steps is set forth for preparing 1α-hydroxy-5,7-dienes from the compounds previously listed.

A. The starting material is oxidized to the 3-ketone-1,4,6-triene.
B. The steroid if it contains hydroxyl or carboxyl groups in the side-chain, is esterified.
C. The ketone is acetylated to form the enol acetate.
D. The enol acetate is reduced to form the 3β-hydroxy-1,5,7-triene.
E. The triazoline dione adduct is formed.
F. The 3β-hydroxyl group is derivatized.
G. The 1,2-epoxy group is introduced.
H. The 3β-hydroxy group is reformed.
I. Reduction is carried out to convert the 1,2-epoxy to 1α-hydroxy and regenerate the 5,7-diene.

Note, however, where the material to be oxidized contains primary or secondary hydroxyls, in addition to the 3-hydroxy group, one may have to protect these groups preferentially or allow them to oxidize and thereafter reduce back to the alcohol.

The following table based upon Example I illustrates schematically the preparation of 1α,25-dihydroxy-7-dehydrocholesterol from 25-hydroxycholesterol.

In both the table and Example I, the numbers identify the starting material, intermediates and end product while the letters identify the reactions.

TABLE

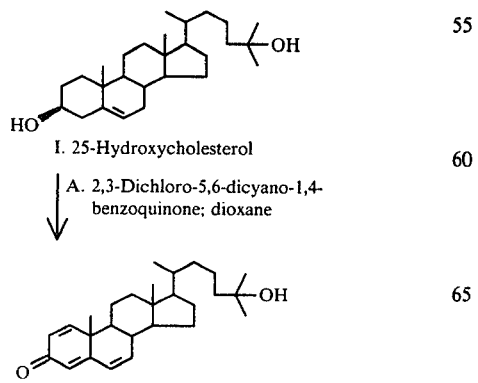

I. 25-Hydroxycholesterol

A. 2,3-Dichloro-5,6-dicyano-1,4-benzoquinone; dioxane

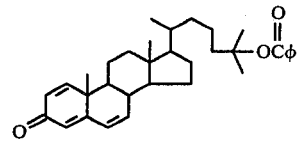

TABLE-continued

II. 25-Hydroxycholesta-1,4,6-trien-3-one

B. Benzoyl chloride; pyridine; dimethylaminopyridine

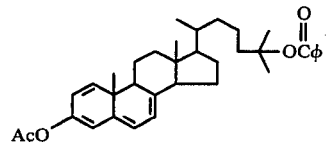

III. 25-Benzoyloxycholesta-1,4,6-trien-3-one

C. Acetic anhydride; acetyl chloride; pyridine

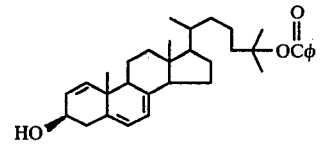

IV. Cholesta-1,3,5,7-tetraene-3,25-diol-3-acetate 25-benzoate

D. Calcium borohydride; ether; methanol; ethanol; water

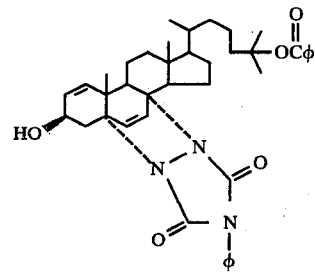

V. Cholesta-1,5-7-triene-3β,25-diol 25-benzoate

E. 4-Phenyl-1,2,4-triazoline-3,5-dione; ethyl acetate; methylene chloride

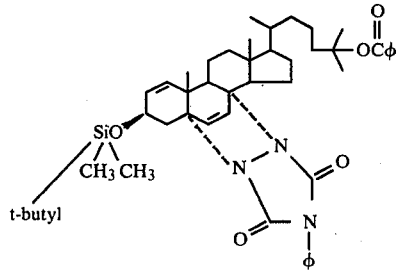

VI. 3',5'-Dioxo-4'-phenyl-5α,8α-(1',2')-1',2',4'-triazolidinocholesta-1,6-diene-3β,25-diol 25-benzoate F. Dimethyl-t-butylsilyl chloride; imidazole; dimethylformamide VII. 3'5'-Dioxo-4'-phenyl-5α,8α,-(1',2')-1',2',4'-triazolidinocholesta-1,6-diene-3β, 25-diol 25-benzoate 3-dimethyl-tert-butylsilyl ether

TABLE-continued

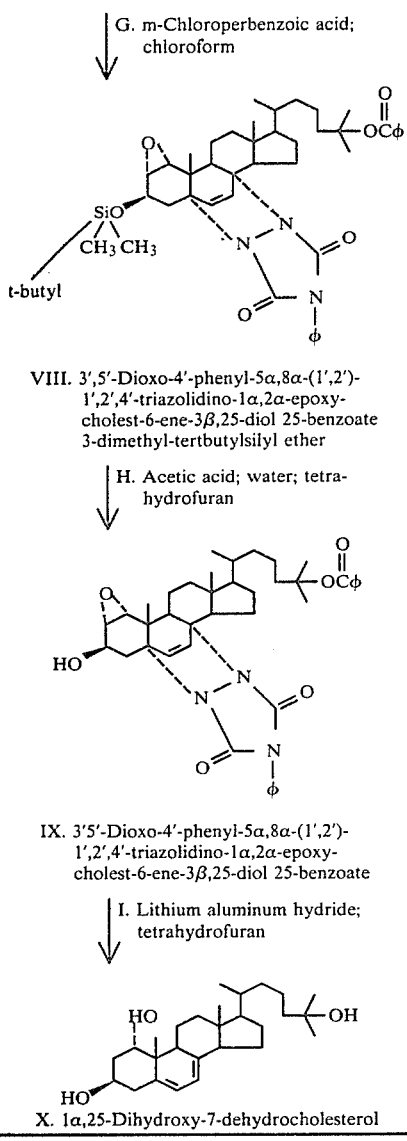

G. m-Chloroperbenzoic acid; chloroform

VIII. 3',5'-Dioxo-4'-phenyl-5α,8α-(1',2')-1',2',4'-triazolidino-1α,2α-epoxy-cholest-6-ene-3β,25-diol 25-benzoate 3-dimethyl-tertbutylsilyl ether H. Acetic acid; water; tetrahydrofuran IX. 3'5'-Dioxo-4'-phenyl-5α,8α-(1',2')-1',2',4'-triazolidino-1α,2α-epoxy-cholest-6-ene-3β,25-diol 25-benzoate I. Lithium aluminum hydride; tetrahydrofuran X. 1α,25-Dihydroxy-7-dehydrocholesterol

DESCRIPTION OF THE PREFERRED EMBODIMENTS

With respect to Step A, oxidation can be achieved by use of any quinone with a high enough oxidation potential using any appropriate aprotic solvent with heating at from about 100° C. to about 120° C. An example of an appropriate quinone is 2,3-dichloro-5,6-dicyano-1,4-benzoquinone. Examples of aprotic solvents are ethers such as tetrahydrofuran and dioxane. Aliphatic and aromatic solvents can also be utilized. Generally, the quinone is present in amounts of about three to about four molar equivalents.

With respect to Step B, esterification can be achieved by use of any acyl or aroyl halide or anhydride such as acetyl chloride, benzoyl chloride and acetic anhydride in pyridine, aromatic (benzene, toluene), aliphatic (pentane, hexane), chlorocarbon or ether solvent with or without catalysts such as dimethylaminopyridine at room temperature or above. Esterification is, of course, only employed where the steroid has a terminal hydroxyl or carboxylic acid group on the side-chain such as in the case of 25-hydroxycholesterol and cholenic acid. The esterifying agent is employed in amounts of about one to about five molar equivalents.

With respect to Step C, enol esterification can be achieved by use of any sufficiently electrophilic acylating agent such as acetic anhydride, acetyl chloride, trifluoroacetyl chloride or anhydride, trichloroacetyl chloride or anhydride, isopropenyl acetate or its perfluorinated or perchlorinated derivatives. The reaction can be carried out with warming to reflux with or without pyridine which controls acidity. The quantity of acylating agent can be from about one to about twenty molar equivalents and where acetic anhydride is present it is present in an amount of about 20 to about one hundred molar equivalents.

With respect to Step D, reduction can be achieved by any borohydride reducing agent such as sodium, potassium, lithium or calcium borohydride, cyanoborohydride or sulfurated borohydride, or aluminum hydride such as lithium aluminum hydride, sodium bis(2-methoxyethoxy)-aluminum hydride, lithium diisopropylaluminum hydride in any appropriate aprotic solvent such as toluene, tetrahydrofuran or ethyl ether at about −5° to about 25° C. The amount of reducing agent is about ten to about twenty molar equivalents.

With respect to Step E, additon of 4-phenyl-1,2,4-triazoline-3,5-dione can be achieved dissolved in any suitable solvent such as methylene chloride, chloroform, acetone, ethyl acetate, etc. at about 0° to about 25° C. There is used a molar equivalent or slight excess of triazoline dione.

With respect to Step F, the 3β-alcohol is derivatized with any bulky ether-forming reagent, such as dimethyl-t-butylsilyl halide, or bulky ester forming group such as pivaloyl halide in any appropriate aprotic solvent such as pyridine, dimethylformamide, etc. at room temperature to about 50° C. There is used about one to about five molar equivalents of ether forming reagent. This directs α-epoxidation in the next step by hindering β-epoxidation.

With respect to step G, the 1,2-epoxy group is introduced by reaction with from about a three to about a ten fold molar excess of any appropriate percarboxylic acid, e.g., peracetic, perbenzoic, m-chloroperbenzoic, or perphthalic acid in any appropriate nonolefinic solvent such as methylene chloride, chloroform or diethyl ether at room temperature to about 50° C.

With respect to Step H, desilylation to reform the 3β-hydroxy group can be achieved with an organic acid (acetic, trifluroacetic), or tetrasubstituted ammonium fluoride in an appropriate solvent such as water and tetrahydrofuran at room temperature or higher. If an ester forming reagent is used instead, it can be removed by hydrolysis or reduction.

With respect to Step I, reduction to convert the 1,2-epoxy group to 1α-hydroxy and to regenerate the 5,7-diene can be achieved with any aluminum hydride such as lithium aluminum hydride, sodium-bis-(2-methoxyethoxy)-aluminum hydride or diisopropyl aluminum hydride in any aprotic solvent such as ethers (diethyl ether, tetrahydrofuran) or aromatic hydrocarbons (toluene, benzene) at room temperature to reflux using from about a 2 to about a 30 fold molar excess of reducing agent.

For a fuller understanding of this invention, reference may be made to the following examples. These examples are given merely to illustrate the invention and are not to be construed in a limiting sense.

EXAMPLE I

This example is directed to the preparation of 1α,25-dihydroxy-7-dehydrocholesterol from 25-hydroxycholesterol.

(A) 25-HYDROXYCHOLESTA-1,4,6-TRIEN-3-ONE (II)

25-Hydroxycholesterol (I) (10.0 gm, 0.0248 mol) was dissolved in 290 ml of dry dioxane. 2,3-Dichloro-5,6-dicyano-1,4-benzoquinone (18.62 gm, 0.082 mol) was added and the reaction was refluxed 14 hours. The reaction mixture was allowed to cool and then filtered. The filtrate was concentrated, in vacuo, to give 14.7 gm red-brown solid. This solid was taken up in 40 ml ethyl acetate and chromatographed on 250 gm neutral alumina, eluting with ethyl acetate. Product-containing fractions were combined, concentrated and recrystallized from 50 ml ethyl acetate giving 5.80 g of the title compound (58%): m.p. 179.5°–181.5° C.; nmr (CDCl$_3$): δ0.76 (s,3H,C$_{19}$CH$_3$), 1.20 (s,9H,C$_{18}$+C$_{26}$+C$_{27}$CH$_3$'s), 2.04 (s,1H,OH), 6.10 (m,4H,C$_2$+C$_4$+C$_6$+C$_7$H's), 7.10 (d,J=12 Hz, 1H,C$_1$H); UV (ethanol) λmax 225, 257, 299 nm.

(B) 25-BENZOYLOXYCHOLESTA-1,4,6-TRIEN-3-ONE (III)

25-Hydroxycholesta-1,4,6-trien-3-one (II) (4.1 gm, 0.0104 mol) was dissolved in 37 ml pyridine containing a catalytic amount of dimethylaminopyridine (100 mg). 1.80 ml of benzoyl chloride (2.18 gm, 0.0155 mol) was added dropwise over a 30 minute period. The reaction mixture was then stirred at 50° C. for 14 hours. The reaction was quenched by decanting into 500 ml water and extracted three times with 100 ml methylene chloride which was washed 5 times with 50 ml 3 N HCl, 2 times with 100 ml distilled water, neutralized with saturated aqueous sodium bicarbonate, filtered and concentrated, in vacuo, to give 7.0 gm of crude red oil. This material was adsorbed onto 10 gm silica gel and chromatographed over 110 gm silica gel, using an ethyl acetate/hexane gradient. Product containing fractions were combined and concentrated, in vacuo, giving 3.95 gm of the desired benzoate ester (77%): m.p. 131.5°–133° C.; nmr (CDCl$_3$) δ0.74 (s,3H,C$_{18}$CH$_3$), 1.60 (s,6H,C$_{26}$+C$_{27}$CH$_3$'s), 6.16 (m, 4H, C$_2$+C$_4$+C$_6$+C$_7$H's), 7.16 (d,J=12 Hz, 1H, C$_1$H), 7.50 (m, 3H, ArH), 8.08 (m,2H,ArH); UV (ethanol) λmax 228,257, 298 nm.

(C) CHOLESTA-1,3,5,7-TETRAENE-3,25-DIOL 3-ACETATE 25-BENZOATE (IV)

25-Benzoyloxycholesta-1,4,6-trien-3-one (III) (3.95 gm, 0.0079 mol) was dissolved in 24.2 ml acetic anhydride (26.14 gm, 0.26 mol), 10.5 ml acetyl chloride (10.92 gm, 0.14 mol) and 1.1 ml pyridine (1.08 gm, 0.014 mol). The solution was then refluxed under nitrogen for 3 hours. The warm product solution was pipetted into 500 ml of an excess of solid sodium bicarbonate in saturated aqueous sodium bicarbonate. After stirring for 1 hour, the thick oily gum was extracted into 250 ml methylene chloride. The methylene chloride solution was washed 2 times with saturated aqueous sodium bicarbonate, 2 times with distilled water, separated, filtered, and concentrated in vacuo affording 4.1 gm of crude enolacetate which was reduced without further purification (95.8%). Product failed to crystallize from a variety of solvents. nmr (CDCl$_3$):δ0.74 (s,3H,C$_{19}$C$_3$), 1.16 (s,3H,C$_{18}$CH$_3$), 1.60 (s,6H,C$_{26}$+C$_{27}$CH$_3$'s), 5.68 (m,2H), 5.94 (brs, 3H); UV (ethanol)λmax 254, 358 nm.

(D) CHOLESTA-1,5,7-TRIENE-3β,25-DIOL 25-BENZOATE (V)

Cholesta-1,3,5,7-tetraene-3,25-diol 3-acetate 25-benzoate (IV) (4.1 gm, 0.0076 mol) was dissolved in ethyl ether and chilled to ca −10° C. Calcium chloride (11.54 gm, 0.103 mol) was dissolved in 268 ml methanol and chilled to ca −10° C. in an ice acetone cold bath. Sodium borohydride (15.75 gm, 0.152 mol) was dissolved in 328 ml ethanol, chilled to ca 10° C. and added dropwise to the calcium chloride solution. The solution was stirred for 15 minutes and then 10 ml water was added. The chilled solution of enol acetate was then added dropwise to the borohydride solution. Following addition, the reaction mixture was stirred at 0° C. for 1.5 hours. The reaction was quenched by the dropwise addition of 100 ml acetone and then concentrated in vacuo to dryness. Solids were dissolved in 150 ml glacial acetic acid, 100 ml water and 500 ml methylene chloride. The methylene chloride phase was separated and washed 3 times with 100 ml saturated aqueous sodium bicarbonate, 3 times with 100 ml distilled water, filtered and concentrated in vacuo to give 3.8 gm of the title compound as an amber glassy solid which was used without further purification (99.7%): nmr (CDCl$_3$)δ4.24 (br s, 1H,C$_{3\alpha}$H), 5.46 (br s, 1H), 5.70 (br s, 3H), 7.50 (m,3H,ArH), 8.08 (m,2H,ArH); UV (ethanol)λmax 228, 271, 281, 292 nm.

(E) 3',5'-DIOXO-4'-PHENYL-5α,8α-(1',2')-1',2',4'-TRIAXZOLIDINOCHOLESTA-1,6-DIENE-3β,25-DIOL 25-BENZOATE (VI)

Cholesta-1,5,7-triene-3β,25-diol 25-benzoate (V) (3.81 gm, 0.0076 mol) was dissolved in 80 ml methylene chloride. 4-Phenyl-1,2,4-triazoline-3,5-dione (1.33 gm, 0.0076 mol) was dissolved in 25 ml ethyl acetate and added dropwise at room temperature to the steroid solution until the red color persisted for more than a minute (0.83 equivalents taken up). The product solution was then concentrated in vacuo and purified by chromatography on 75 gm silica gel using an acetone/hexane gradient to give 4.50 gm of Diels-Alder adduct (90%): m.p. 119°–122° C., nmr (CDCl$_3$)α0.74(s,3H,C$_{18}$CH$_3$) 1.20 (s,3H,C$_{19}$CH$_3$) 1.56 (s,C$_{26}$+C$_{27}$CH$_3$'s), 3.22 (m,1H,C$_{9\alpha}$H), 5.02 (m,1H,C$_{3\alpha}$H), 5.70 (s,2H,C$_1$+C$_2$H's), 6.24 and 6.44 (AB quartet, J=8 Hz,2H,C$_6$+C$_7$H's), 7.38 (s,5H,ArH), 7.50 (m,3H,ArH), 8.06 (m,2H,ArH).

(F) 3',5'-DIOXO-4'-PHENYL-5α,8α-(1',2')-1',2',4'-TRIAZOLIDINOCHOLESTA-1,6-DIENE-3β,25-DIOL 25-BENZOATE 3-DIMETHYL-TERT-BUTYLSILYL ETHER (VII)

3',5'-Dioxo-4'-phenyl-5α,8α-(1',2')-1',2',4'-triazolidinocholesta-1,6-diene-3β,25-diol 25-benzoate (VI) (1.95 gm, 0.00288 mol) was dissolved in 5 ml dimethylformamide and warmed in an oil bath at 40° C. Imidazole (0.706 gm, 0.0104 mol) was added, followed by dimethyl-tert-butylsilyl chloride (0.707 gm, 0.0047 mol). After 15 minutes the reaction was quenched by pouring into 300 ml distilled water. The product was extracted with 250 ml methylene chloride, washed 3 times with 100 ml distilled water, filtered and concentrated in vacuo. The crude product was purified by absorption onto silica gel and chromatographing over 25 gm silica gel using an acetone/hexane gradient to give 2.0 gm pure silyl ether (88%): m.p. 151°–154° C.; nmr (CDCl$_3$)α0.06 and 0.12 (s,6H,Si(CH$_3$)$_2$), 0.92 (s,9H,t-Bu), 1.60 (s,6H,C$_{26}$+C$_{27}$CH$_3$'s), 3.34 (m,1H,C$_{9\alpha}$H), 5.00 (m,1H,C$_{3\alpha}$H), 5.70 (s,2H,C$_1$+C$_2$H's), 6.28 and 6.44 AB quartet, J=8 Hz, 2H,C$_6$+C$_7$H's), 7.40 (s,5H,ArH), 7.50 (m,3H,ArH), 8.02 (m,2H,ArH).

(G)
3',5'-DIOXO-4'-PHENYL-5α,8α-(1',2')-1',2',4'-TRIAZOLIDINO-1α,2α-EPOXYCHOLEST-6-ENE-3β,25-DIOL 25-BENZOATE 3-DIMETHYL-TERT-BUTYLSILYL ETHER (VIII)

3',5'-Dioxo-4'-phenyl-5α,8α-(1',2')-1',2',4'-triazolidinocholesta-1,6-diene-3β,25-diol 25-benzoate-3-dimethyl-tert-butylsilyl ether (VII) (0.4 gm, 0.000505 mol) was dissolved in 10 ml chloroform. m-Chloroperbenzoic acid (0.22 gm, 0.00126 mol was added and the reaction mixture stirred at room temperature for 24 hours. More m-chloroperbenzoic acid (0.22 gm, 0.00126 mol) was added and the reaction mixture stirred for an additional 24 hours. Again, more m-chloroperbenzoic acid (0.11 gm, 0.00064 mol) was added and the reaction mixture stirred for 17 hours longer. The reaction was terminated by pouring into 100 ml of 10% aqueous potassium carbonate solution. The chloroform phase was separated, diluted with 100 ml methylene chloride, washed 2 times with 50 ml 10% aqueous potassium carbonate, 2 times with 100 ml distilled water, filtered and concentrated in vacuo to give 0.50 gm of a clear glassy solid. Chromatography over 20 gm silica gel using an acetone/hexane gradient afforded 0.33 gm of pure epoxide (81%): m.p. 176°–179° C.; nmr (CDCl$_3$)α0.16 (s,6H,Si(CH$_3$)$_2$), 0.92 (s,9H,t-Bu), 1.22 (s,3H,C$_{19}$CH$_3$), 1.56 (s,6H,C$_{26}$+C$_{27}$CH$_3$'s), 3.18 (m,3H,C$_{1\beta}$+C$_{2\beta}$+C$_{9\alpha}$H's), 4.98 (m,1H,C$_{3\alpha}$H), 6.20 and 6.46 (AB quartet, J=8 Hz,2H,C$_6$+C$_7$H's), 7.40 (m,8H,ArH), 8.00 (m,2H,ArH).

(H)
3',5'-DIOXO-4'-PHENYL-5α,8α-(1',2')-1',2',4'-TRIAZOLIDINO-1α,2α-EPOXYCHOLEST-6-ENE-3β,25-DIOL 25-BENZOATE (IX)

3',5'-Dioxo-4'-phenyl-5α,8α-(1',2')-1',2',4'-triazolidino-1α,2α-epoxycholest-6-ene-3β,25-diol 25-benzoate 3 dimethyl-tert-butylsilyl ether (VIII) (1.50 gm, 0.00186 mol) was dissolved in 22 ml tetrahydrofuran, 22 ml glacial acetic acid and 11 ml distilled water and stirred in an oil bath at 45°–48° C. for 5 days. The reaction was quenched by the dropwise addition to 250 ml saturated aqueous sodium bicarbonate. The product was extracted into 200 ml methylene chloride and the solution washed 3 times with 100 ml saturated aqueous sodium bicarbonate, filtered and concentrated in vacuo to give 1.4 gm tan solid. This material was chromatographed over 40 gm silica gel using an ethyl acetate/hexane gradient affording 0.19 gm of starting material and 1.09 gm pure epoxy alcohol (99%): m.p. 130°–133° C.; nmr (CDCl$_3$)α1.20 (s,3H,C$_{19}$CH$_3$), 1.58 (s,6H,C$_{26}$+C$_{27}$CH$_3$'s), 3.14 (s,2H,C$_{1\beta}$+C$_{2\beta}$H's), 3.72 (br s, 1H,OH), 5.00 (m,1H,C$_{3\alpha}$H), 6.14 and 6.40 (AB quartet, J=8 Hz,2H,C$_6$+C$_7$H's), 7.40 (m,8H,ArH), 8.00 (m,2H,ArH).

(I)
1α,25-DIHYDROXY-7-DEHYDROCHOLESTEROL (X)

3',5'-Dioxo-4'-phenyl-5α,8α-(1',2')-1',2',4'-triazolidino-1α,2α-epoxycholest-6-ene-3β,25-diol 25-benzoate (IX) (1.04 gm, 0.0015 mol) was dissolved in 50 ml tetrahydrofuran. Lithium aluminum hydride (1.14 gm, 0.030 mol) was added to 50 ml tetrahydrofuran chilled to 0° C. The steroid solution was then added dropwise to the hydride solution. The ice bath ws removed and the reaction mixture gently warmed to reflux under nitrogen for 90 minutes. The reaction mixture was then chilled and the reaction quenched by the dropwise addition of 1.14 ml water, 1.14 ml 15% aqueous potassium hydroxide and 3.42 ml of water. The cold bath was removed and the slurry was stirred for 15 minutes and then filtered on a buchner funnel. The solids were washed 3 times with 100 ml tetrahydrofuran and the combined filtrates concentrated, in vacuo, to give 0.94 gm of clear oil. This material was purified by chromatography over 40 gm silica gel using an ethyl acetate/hexane gradient to give 0.60 gm of pure 1α,25-dihydroxy-7-dehydrocholesterol (96.8%): m.p.: 150°–153° C.; nmr (CDCl$_3$)α0.60 (s,3H,C$_{18}$CH$_3$), 1.20 (s,6H,C$_{26}$+C$_{27}$H's),3.74 (br s,1H,C$_{1\beta}$H), 3.98 (m,1H,C$_{3\alpha}$H),5.40 and 5.72 (m,2H,C$_6$+C$_7$H's); UV (ethanol)λmax 271, 282, 294 nm.

EXAMPLE II

This example is directed to a sequence of steps starting with the enol acetylation of cholesta-1,4,6-trien-3-one obtained from cholesterol and ending with the protection of the 3-hydroxyl group by reaction with dimethyl-t-butylsilyl chloride. For convenience, the reaction steps are labeled in accordance with the previously described sequence of steps.

(C) CHOLESTA-1,3,5,7-TETRAEN-3-YL ACETATE

Cholesta-1,4,6-trien-3-one (1.5 gm, 0.0039 mol) was dissolved in 12.09 ml acetic anhydride (13.05 gm, 0.13 mol), 5.19 ml acetyl chloride (5.40 gm, 0.069 mol) and 0.54 ml pyridine (0.53 gm, 0.0067 mol). The solution was refluxed under nitrogen for 2 hours; then poured into 300 ml of ice water. After stirring 30 minutes, the solid was filtered off, washed with 300 ml saturated aqueous sodium bicarbonate, 500 ml distilled water and air dried. Recrystallization from 25 ml ethanol afforded 1.4 gm of pure enol acetate (84.3%): m.p. 122°–124° C.; nmr (CDCl$_3$)α0.62 (s,3H,C$_{18}$CH$_3$), 0.82 (s,3H,C$_{19}$CH$_3$), 0.92 (s,6H,C$_{26}$+C$_{27}$CH$_3$'s), 2.18 (s,3H,OAc), 5.68 (m,2H), 5.94 (m,3H); UV (ethanol)λmax 254, 357 nm.

(D) CHOLESTA-1,5,7-TRIEN-3β-OL

Sodium borohydride (1.2 gm, 0.032 mol) was dissolved in 64 ml ethanol. Anhydrous calcium chloride (2.4 gm, 0.022 mol) was dissolved in 56 ml methanol, and added to the borohydride solution. Cholesta-1,3,5,7 tetraen-3-yl acetate (0.80 gm, 0.0019 mol) was dissolved in 80 ml ethyl ether and added to the chilled borohydride solution. The solution was then stirred at −3° to 0° C. for 3 hours. The reaction was then quenched by the addition of 25 ml acetone and the product mixture concentrated in vacuo to dryness. Solids were taken up in 50 ml glacial acetic acid, 50 ml water and 150 ml methylene chloride. The methylene chloride phase was separated, washed 3 times with 50 ml saturated aqueous sodium bicarbonate, 3 times with 50 ml distilled water, filtered and concentrated, in vacuo. Crystallization from methanol afforded 0.65 gm of pure 1,5,7-triene (89.7%): m.p. 128°–129° C.; nmr (CDCl$_3$)α0.67 (s,3H,C$_{18}$CH$_3$), 0.90 (d,J=6 Hz,3H,C$_{21}$CH$_3$), 1.0 (d,J=8 HZ,6H,C$_{26}$+C$_{27}$CH$_3$'s), 1.50 (s,3H,C$_{19}$CH$_3$), 4.30 (m,1H), 5.45 (br s, 1H) 5.67 (br s, 3H); UV (ethanol)λmax 271, 281, 292 nm.

(E)
3',5'-DIOXO-4'-PHENYL-5α,8α-(1',2')-1',2',4'-TRIAZOLIDINOCHOLESTA-1,6-DIEN-3β-OL

Cholesta-1,5,7-trien-3β-ol (0.29 gm, 0.00076 mol) was dissolved in 8 ml methylene chloride. 4-Phenyl-1,2,4-triazoline-3,5-dione (0.133 gm, 0.00076 mol) was dissolved in 5 ml ethyl acetate and added dropwise at room temperature to the steroid solution until the red color persisted for more than a minute (0.7 equivalents taken up). The product solution was then concentrated in vacuo to give 0.41 gm of Diels-Alder adduct (97%): m.p. 175°–178° C.; nmr (CDCl$_3$) α0.81 (s,3H,C$_{18}$CH$_3$), 0.86 (d,J=6,6H,C$_{26}$+C$_{27}$CH$_3$), 3.34 (dd, J=14 and 7 Hz,1H,C$_{9\alpha}$H), 5.02 (t,J=6 Hz,1H,C$_{3\alpha}$H), 5.70 (s,3H,C$_1$+C$_2$H's), 6.44 and 6.24 (AB quartet, J=8 Hz,2H,C$_6$+C$_7$H's), 7.38 (m,5H,ArH).

(F)
3',5'-DIOXO-4'-PHENYL-5α,8α-(1',2')-1',2',4'-TRIAZOLIDINOCHOLESTA-1,6-DIEN-3β-OL 3-DIMETHYL-TERT-BUTYLSILYL ETHER

3',5'-Dioxo-4'-phenyl-5α,8α-(1',2')-1',2',4'-triazolidinocholesta-1,6-diene-3β-ol (0.41 gm, 0.000736 mol) was dissolved in 2 ml dimethylformamide and warmed in an oil bath at 45° C. Imidazole (0.180 gm, 0.00265 mol, 3.6 eq) was added, followed by dimethyl-tert-butylsilyl chloride (0.181 gm, 0.0012 mol, 1.63 eq). After 15 minutes the reaction was quenched by pouring into 100 ml of distilled water. The product was extracted 3 times with 100 ml methylene chloride. To completely extract the emulsion which had formed, the methylene chloride-water-dimethylformamide mixture was allowed to separate overnight in a separatory funnel. The combined methylene chloride solutions were washed 4 times with 250 ml water, dried (Na$_2$SO$_4$), filtered, and concentrated in vacuo to give 0.50 gm of crude silyl ether. The crude product was purified by chromatography over 20 gm of silica gel, using an acetone/hexane gradient. Product-containing fractions were combined to give 0.40 gm of pure silyl ether (82%): m.p. 159°–161° C., nmr (CDCl$_3$)α0.10 (s,6H,Si(CH$_3$)$_2$), 0.80 (s,3H,C$_{18}$CH$_3$), 0.90 (s,9H,t-butyl), 1.08 (s,3H,C$_{19}$CH$_3$), 3.34 (dd,J=14 and 8 Hz,1H,C$_{9\alpha}$H), 4.98 (t,J=7 Hz,C$_{3\alpha}$H), 5.70 (s,2H,C$_1$+C$_2$H's), 6.24 and 6.44 (AB quartet, J=6 Hz,2H, C$_6$+C$_7$H's), 7.40 (m,5H,ArH).

(G)
3=,5'-DIOXO-4'-PHENYL-5α,8α-(1',2')-1',2',4'-TRIAZOLIDINO-1α,2α-EPOXYCHOLEST-6-EN-3β-OL 3-DIMETHYL-TERT-BUTYLSILYL ETHER

3',5'-Dioxo-4'-phenyl-5α,8α-(1',2')-1',2',4'-triazolidinocholesta-1,6-dien-3β-ol 3-dimethyl-tert-butylsilyl ether (0.29 gm, 0.00043 mol) was dissolved in 7 ml chloroform. m-Chloroperbenzoic acid (0.187 gm, 0.00108 mol, 2.5 eq) was added and the reaction mixture stirred at room temperature for 24 hours. More m-chloroperbenzoic acid (0.1987 gm, 0.00108 mol, 2.5 eq) was added and the reaction mixture was stirred for an additional 44 hours. The reaction was quenched by pouring into 100 ml of 10% aqueous potassium carbonate. The chloroform phase was diluted with 100 ml methylene chloride, separated, washed 3 times with 100 ml 10% aqueous potassium carbonate, filtered and concentrated in vacuo to give 0.3 gm clear glassy solid. Chromatography over 20 gm silica gel using an acetone/hexane gradient to give 0.27 gm of pure epoxide: (89%): m.p. 155°–158° C.; nmr (CDCl$_3$) α0.12 (s,6H,SiMe$_2$), 0.80 (s,3H,C$_{18}$CH$_3$), 0.92 (s,9H,t-butyl), 3.18 (m,3H,C$_{1\beta}$+C$_{2\beta}$+C$_{9\beta}$H's), 4.94 (t,J=7 Hz,1H,C$_{3\beta}$H,) 6.46 and 6.20 (AB quartet, J=7 Hz,2H,C$_6$+C$_7$H's), 7.42 (m,5H,ArH).

EXAMPLE III

This example is directed to a sequence of steps starting with the enol acetylation of methyl-3-ketochola-1,4,6-trien-24-oate, the methyl ester of cholenic acid. For convenience, the reaction steps are labeled in accordance with the previously described sequence of steps.

(C) METHYL 3-ACETOXYCHOLA-1,3,5,7-TETRAEN-24-OATE

Methyl 3-ketochola-1,4,6-trien-24-oate (2.0 gm, 0.0052 mol) was dissolved in 16.07 ml acetic anhydride (17.36 gm, 0.17 mol), 6.85 ml of acetyl chloride (7.12 gm, 0.091 mol) and 0.71 ml of pyridine (0.69 gm, 0.0088 mol). The reaction mixture was then refluxed under nitrogen for 3 hours and then quenched by pouring into 500 ml of ice water with vigorous stirring. After stirring for 30 minutes the solid was removed by filtration and washed with 500 ml of saturated aqueous sodium bicarbonate, then with 500 ml of distilled water and air dried. Crystallization from 12 ml ethanol yielded 1.69 gm of pure enol acetate (77%): m.p. 106°–111° C.; nmr (CDCl$_3$)α2.12 (s,3H,OAc), 3.70 (s,3H,CO$_2$CH$_3$), 5.54 (m,2H), 5.78 (m,3H), UV (ethanol)λmax 240, 358 nm.

(D)
METHYL-3β-HYDROXYCHOLA-1,5,7-TRIEN-24-OATE

Sodium borohydride (1.80 gm, 0.0475 mol) was dissolved in 96 ml ethanol and chilled to 0° C. Calcium chloride (3.61 gm, 0.0325 mol) was dissolved in 84 ml methanol and added to the borohydride solution. Methyl-3-acetoxychola-1,3,5,7-tetraen-24-oate (1.20 gm, 0.00283 mol) was dissolved in 150 ml diethylether and added dropwise to the chilled borohydride solution. Following addition, the solution was stirred at 0° C. for 3 hours. The reaction was quenched by the dropwise addition of 100 ml acetone and the solution was concentrated in vacuo. Solids were dissolved in 25 ml glacial acetic acid, 200 ml water and 300 ml methylene chloride. The methylene chloride was washed 3 times with 100 ml distilled water, neutralized with saturated aqueous sodium bicarbonate, filtered and concentrated in vacuo to give 1.09 gm of crude 1,5,7-triene. The product failed to crystallize from a variety of solvents: nmr (CDCl$_3$)α3.70 (s,3H,CO$_2$CH$_3$), 4.24 (m,1H,C$_{3\alpha}$H) (br s,1H), 5.70 (br s,3H); UV (ethanol) λmax 225, 272, 282, 293 nm.

While the invention has been described with reference to certain specific embodiments thereof, it is understood that it is not to be so limited since alterations and changes may be made therein which are within the full intended scope of the appended claims.

What is claimed is:

1. A steroid compound having the structure:

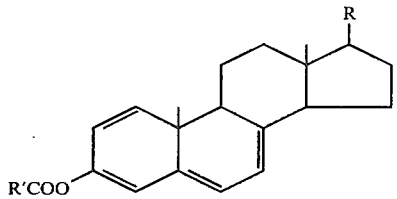

where R is selected from the group consisting of $C_8H_{16}OH$; $C_8H_{16}O_2CCH_3$;

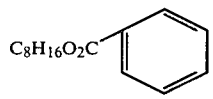

and $C_5H_8O_2CH_3$ and where R'CO— is the residue of an acylating agent.

2. Cholesta-1,3,5,7-tetraene-3,25-diol 3-acetate 25-benzoate.

3. Methyl 3-acetoxychola-1,3,5,7-tetraen-24-oate.

4. An enol acetylation process comprising reacting a steroid containing:

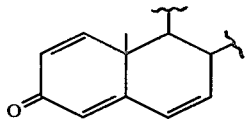

with an acylating agent forming the corresponding Δ1,3,5,7-Tetraene-enol acetate.

5. The process of claim 4 wherein said acylating agent is present in an amount of from about one to about twenty molar equivalents with the proviso that where acetic anhydride is present, it is present in an amount of from about twenty to about one hundred molar equivalents.

6. The process of claim 4 wherein pyridine is present.

7. The process of claim 4 wherein acetic anhydride and acetyl chloride are present.

8. An enol acetylation process comprising reaction with an acylating agent to form the corresponding Δ1,3,5,7-Tetraene-enol acetate a steroid of the following structure:

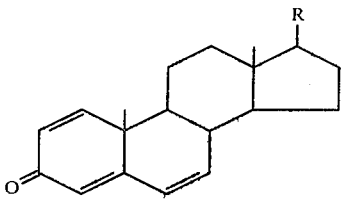

where:

R is $$R \text{ is } \underset{}{\overset{}{\diagdown}}(CH_2)_aZ,$$

Z is
$$-\underset{CH_3}{\overset{CH_3}{\underset{|}{C}}}-H, \quad -\underset{}{\overset{CH_3}{\underset{|}{C}}}-\underset{CH_2-OCR'}{\overset{O}{\underset{\parallel}{OCR'}}}$$

and where Z is the above, a is 3,

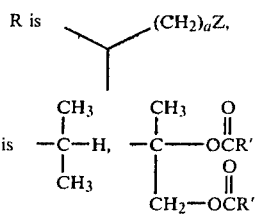

and where Z is the above, a is 0, 1, 2 or 3,

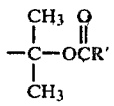

and where Z is the above, a is 2, and

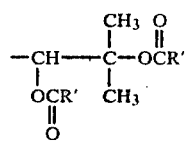

and where Z is the above, a is 0, 1, 2 or 3, and R' is hydrogen, alkyl or aryl.

9. The process of claim 8 wherein said acylating agent is present in an amount of from about one to about twenty molar equivalents with the proviso that where acetic anhydride is present, it is present in an amount of from about twenty to about one hundred molar equivalents.

10. The process of claim 8 wherein pyridine is present.

11. The process of claim 8 wherein acetic anhydride and acetyl chloride are present.

12. The process of claim 8 wherein said steroid is cholesta-1,4,6-trien-3-one.

13. The process of claim 8 wherein said steroid is 25-benzyloxycholesta-1,4,6-trien-3-one.

14. The process of claim 8 wherein said steroid is methyl 3-ketochola-1,4,6-trien-24-oate.

* * * * *